(12) United States Patent
Lambert

(10) Patent No.: US 8,049,174 B2
(45) Date of Patent: Nov. 1, 2011

(54) CHEMICAL VAPOR SENSOR SYSTEM AND METHOD THEREOF

(75) Inventor: David K. Lambert, Sterling Heights, MI (US)

(73) Assignee: Delphi Technologies, Inc., Troy, MI (US)

( * ) Notice: Subject to any disclaimer, the term of this patent is extended or adjusted under 35 U.S.C. 154(b) by 583 days.

(21) Appl. No.: 12/287,103

(22) Filed: Oct. 6, 2008

(65) Prior Publication Data

US 2009/0272174 A1 Nov. 5, 2009

Related U.S. Application Data

(60) Provisional application No. 61/050,426, filed on May 5, 2008.

(51) Int. Cl.
*G01J 5/02* (2006.01)
(52) U.S. Cl. ...................................................... 250/343
(58) Field of Classification Search .......... 250/330–335, 250/336.1–336.2, 338.1–338.5, 339.01–339.15, 250/340, 341.1–341.8, 342–353; 600/529, 600/532, 543; 73/23.3
See application file for complete search history.

(56) References Cited

U.S. PATENT DOCUMENTS

| | | | |
|---|---|---|---|
| 3,792,272 A | | 2/1974 | Harte et al. |
| 4,268,751 A | * | 5/1981 | Fritzlen et al. ................ 250/343 |
| 4,671,298 A | * | 6/1987 | Babb et al. .................... 600/532 |
| 4,905,498 A | * | 3/1990 | O'Donnell et al. ........... 73/23.35 |
| 5,376,555 A | * | 12/1994 | Forrester et al. .............. 436/132 |
| 6,313,464 B1 | | 11/2001 | Schrader |
| 6,811,751 B1 | | 11/2004 | Olsson et al. |
| 7,095,501 B2 | | 8/2006 | Lambert et al. |
| 7,279,132 B2 | | 10/2007 | Sultan et al. |
| 2007/0077176 A1 | * | 4/2007 | Lambert et al. ............ 422/82.05 |
| 2007/0296601 A1 | | 12/2007 | Sultan et al. |
| 2009/0087920 A1 | * | 4/2009 | Pettersson et al. ........... 436/132 |

FOREIGN PATENT DOCUMENTS

| | | |
|---|---|---|
| EP | 0633471 | 1/1995 |
| EP | 1441212 | 7/2004 |
| JP | 2002241313 | 9/2000 |
| WO | 2006055458 | 5/2006 |

OTHER PUBLICATIONS

David K. Lambert et al., "Passive Sensing of Driver Intoxication," Shanghai Institute of Microsystem and Information Technology, SAE 2006 World Congress (13 pages).

(Continued)

*Primary Examiner* — Kiho Kim
(74) *Attorney, Agent, or Firm* — Jimmy L. Funke

(57) ABSTRACT

A chemical vapor sensor system and method are provided, wherein the system includes an air input device, a light source, a detector, a sample chamber, and a processor. The air input device includes at least a sample input port, a reference input port, and an output port. The light source emits light, and the detector receives at least a portion of the emitted light. The sample chamber is in fluid communication with the output port, wherein the air alternatively enters the air input device from the sample input port and the reference input port and enters the sample chamber. The processor receives an output signal from the detector based upon a detection of at least carbon dioxide and ethanol in the air in the sample chamber, wherein the processor determines a blood alcohol content of a person whose breath was received in the sample input port.

17 Claims, 4 Drawing Sheets

OTHER PUBLICATIONS

Lindberg, L., et al. "Breath alcohol concentration determined with a new analyzer using free exhalation predicts almost precisely the arterial blood alcohol concentration," Elsevier Ireland Ltd., Forensic Science Int'l 168 (2007) pp. 200-207.

Pogodina, O., et al. "Combination of sorption tube sampling and thermal desorption with hollow waveguide FT-IR spectroscopy for atmospheric trace gas analysis: determination of atmospheric ethane at the lower ppb level," Analytical Chemistry, American Chemical Soc'y 76 (2004) 464-468.

Sakakibara, K., et al. "Development of a New Breath Alcohol Detector without Mouthpiece to Prevent Alcohol-Impaired Driving," Intelligent Trans. Sys. Soc'y (2008) Paper Abstract.

* cited by examiner

CHEMICAL VAPOR SENSOR SYSTEM AND METHOD THEREOF

CROSS-REFERENCE TO RELATED APPLICATION

This application claims the benefit under 35 U.S.C. §119(e) of U.S. Provisional Patent Application No. 61/050,426, filed on May 5, 2008, the entire disclosure of which is hereby incorporated herein by reference.

TECHNICAL FIELD

The present invention generally relates to a chemical vapor sensor, and more particularly, to a chemical vapor sensor for measuring carbon dioxide and ethanol.

BACKGROUND OF THE DISCLOSURE

Generally, intoxicated drivers are a major cause of traffic accident fatalities in the United States. A recent National Highway Traffic Safety Administration (NHTSA) report showed that 40% of the total accident fatalities in the U.S. in the year 2003 were alcohol related. More specifically, 12,373 motor vehicle occupants were killed in crashes that involved a blood alcohol concentration (BAC) of 0.08 g/dL or higher. This equates to over 33% of the 37,132 U.S. motor vehicle fatalities in 2003. In addition to the societal impact, the cost of such crashes in the U.S. is about $40 billion per year. It is well established that the rate of fatal traffic accidents per mile traveled is related to a driver's BAC and that there is a correlation between impairment in driving skills and the driver's BAC. The definition of drunk driving in the U.S. involves a BAC level of 0.08 g/dL. A primary countermeasure to combat drunk driving in the U.S. is the criminal justice system, which employs deterrents and sanctions against drunk drivers. Various other approaches to combat drunk driving have been utilized.

One existing approach to combat drunk driving utilizes an electrochemical sensor that measures ethanol concentration in air. Generally, ethanol concentration in human breath is a good indication of BAC. Inside the air sacs in the human lung, there is a chemical equilibrium between the concentration of ethanol in the air and the concentration of ethanol in an individual's blood. For law enforcement purposes, an electrochemical sensor can be built into an object such as a clipboard or flashlight that a police officer can, under certain circumstances, justifiably insert into a vehicle. Electrochemical sensors can also be used in commercially available interlocks, which can be mandated following a driver's drunk driving conviction. However, currently available electrochemical sensors typically have a limited lifetime and typically must be replaced after about three years. Generally, to be used as an on-board component of the safety system, an ethanol sensor must have a lifetime of at least ten to fifteen years. Another electrochemical sensor that can be used includes a device that is pressed against an individual's skin to determine alcohol intoxication through remote detection of ethanol that evaporates from the driver's skin. Other approaches typically involve passing infrared through the driver's extremities, such as a finger, or using Raman spectroscopy to measure the concentration of ethanol in the fluid at the surface of the driver's eyes. Generally, these approaches are impractical for on-board vehicle use as well.

Another approach to combat drunk driving uses a heated film of metal oxide that changes electrical resistance in response to ethanol concentration. Such sensors are sometimes used in handheld devices sold to consumers, typically to self test their BAC. However, such sensors generally operate with undiluted breath from the driver. The breath sample is undiluted and so the detection level needed is only about 210 parts per million (ppm) of ethanol, by volume. Also, the minimum ethanol concentration that can be reliably detected with a metal oxide film is typically in the range of 10 to 50 ppm.

SUMMARY OF THE INVENTION

According to one aspect of the present invention, a chemical vapor sensor system includes an air input device, a light source, a detector, a sample input chamber, and a processor. The air input device includes a plurality of ports including at least a sample input port, a reference input port, and an output port. The light source emits light, and the detector is in optical communication with the light source to receive at least a portion of light emitted from the light source. The sample chamber is in optical communication between the light source and the detector and is in fluid communication with the output port, wherein the air alternatively enters the air input device from the sample input port and the reference input port and enters the sample chamber. The processor receives an output signal from the detector based upon a detection of at least carbon dioxide and ethanol in the air in the sample chamber, wherein the processor determines a blood alcohol content of a person whose breath was received in the sample input port.

According to another aspect of the present invention, a chemical vapor sensor system includes an air input device, an infrared light source, a dual element IR detector, a sample chamber, and a processor. The air input device includes a plurality of ports including at least a sample input port, a reference input port, and an output port. The infrared light source emits IR light, and the dual element IR detector is in optical communication with the IR light source to receive at least a portion of IR light emitted from the light source. The sample chamber is in optical communication between the IR light source and detector, and is in fluid communication with the output port, wherein the air alternatively enters the air input device from the sample input port and reference input port and enters the sample chamber. The processor receives an output signal from the dual element IR detector based upon a detection of carbon dioxide and ethanol in the air in the sample chamber, wherein the processor determines a blood alcohol content (BAC) of a person whose breath was received in the sample input port.

According to yet another aspect of the present invention, a method of detecting chemical vapors includes the steps of alternating air samples between a sample input and a reference input that are inputted into a sample chamber, illuminating a light source, and detecting at least a portion of the light emitted from the light source with a detector, wherein the sample chamber is in optical communication between the light source and the detector. The method further includes the steps of communicating an output from the detector based upon detection of carbon dioxide and ethanol in the air sample, and determining a blood alcohol content of a person whose breath was received in the sample input, wherein the blood alcohol content is based upon the output communicated from the detector.

These and other features, advantages, and objects of the present invention will be further understood and appreciated by those skilled in the art by reference to the following specification, claims, and appended drawings.

BRIEF DESCRIPTION OF THE DRAWINGS

The present invention will now be described, by way of example, with reference to the accompanying drawings, in which.

DESCRIPTION OF PREFERRED EMBODIMENTS

Figure 1:
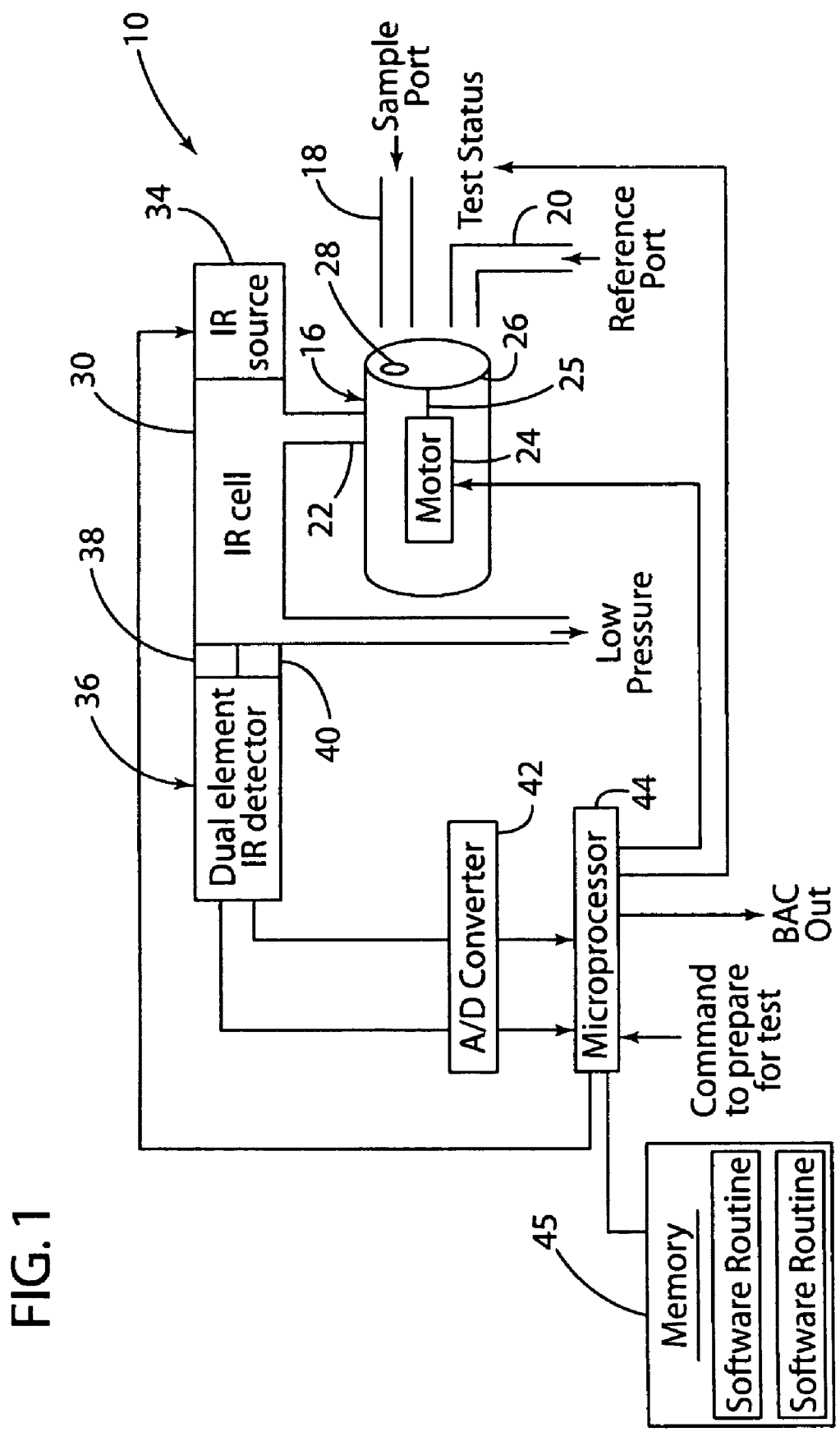
FIG. 1 is a block diagram of a chemical vapor system, in accordance with one embodiment of the present invention.
Figure 2:
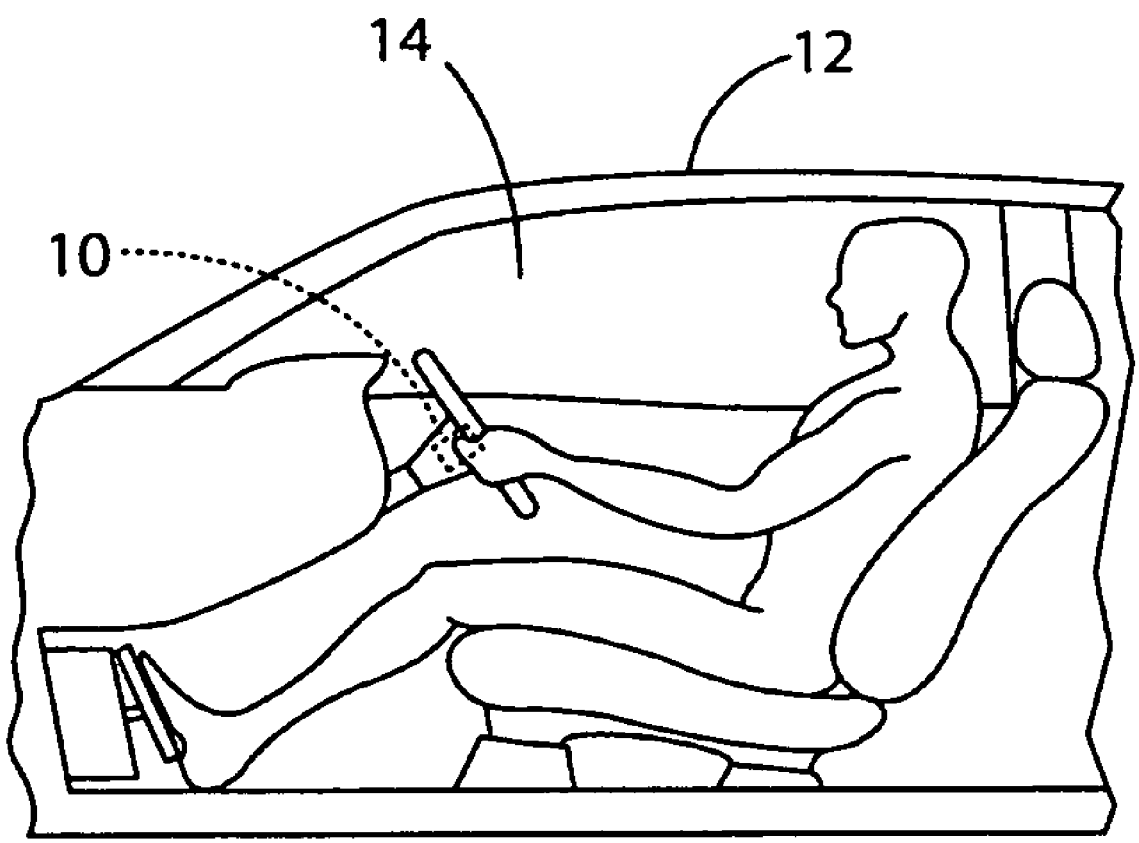
FIG. 2 is an plan-environmental view of a chemical vapor system used in a vehicle, in accordance with one embodiment of the present invention.

In regards to both FIGS. 1 and 2, a chemical vapor sensor system is generally shown in FIG. 1 at reference identifier 10. The chemical vapor sensor 10 measures a suspect chemical species of interest with sensitivity and chemical specificity in a selected area, that can be used with safety systems. According to one embodiment, ethanol is optically detected for on-board use in a motor vehicle 12 (FIG. 2). Ethanol vapor in a vehicle cabin 14 is measured, and sufficient sensitivity is provided to detect that a motor vehicle 12 occupant exceeds the legal limit of blood alcohol concentration (BAC). According to one embodiment, the vehicle occupant whose BAC is being measured is a driver of the vehicle 12. However, it should be appreciated by those skilled in the art that the description herein is not limited to measuring the BAC of the vehicle's 12 driver, but is an exemplary embodiment. Exemplary chemical vapor sensors are disclosed in commonly assigned U.S. Pat. No. 7,279,132 entitled "CHEMICAL VAPOR SENSOR HAVING AN ACTIVE AND A PASSIVE MEASUREMENT MODE," U.S. Patent Application Publication No. 2007/0077176 entitled "TRACER TO COMPENSATE FOR ENVIRONMENTAL VARIATIONS THAT INFLUENCE A CHEMICAL VAPOR SENSOR MEASUREMENT," U.S. patent application Ser. No. 11/243,556 entitled "TRACER TO COMPENSATE FOR ENVIRONMENTAL VARIATIONS THAT INFLUENCE A CHEMICAL VAPOR SENSOR MEASUREMENT," and U.S. patent application Ser. No. 11/033,677 entitled "CHEMICAL VAPOR SENSOR," the entire disclosures of which are hereby incorporated herein by reference.

By way of explanation and not limitation, the threshold of intoxication for legal operation of a vehicle, according to one widely-used legal definition, is when the concentration of ethanol in breath is at or about 0.08 grams of ethanol per two hundred ten (210) liters of breath, which at one (1) atmosphere pressure is equivalent to two hundred ten (210) ppm ethanol by volume. The concentration of ethanol in breath is proportional to the BAC of a person.

Generally, a vapor sensor based on infrared transmission requires an appropriate path length. If the path length is too short, the change in detected intensity is small relative to the fluctuations in detected intensity. If the path length is too long, the detected intensity at the center of an absorption line is small. The optimum path length can depend upon the chemical concentration that is to be measured. Consider, for example, a sensor that measures the fraction of light transmitted in a fixed band of optical frequency. For improved accuracy, the species of interest should maintain on the order of ten percent (10%) absorption in the band. A suitable absorption band to detect ethanol vapor with an incandescent lamp as IR source, is between 2860 cm$^{-1}$ and 3010 cm$^{-1}$ (3.4 µm wavelength), according to one embodiment. For purposes of explanation and not limitation, a suitable IR filter to use is Dexter Research part number FHC1. Near the peak of the 2980 cm$^{-1}$ band, the absorption coefficient is about $2.0\times10^{-4}$ (µmol/mol)$^{-1}$ m$^{-1}$. Consequently, with an ethanol concentration of 250 ppm, a path length of 0.9 m is needed to obtain ten percent (10%) absorption. At the threshold of intoxication, the concentration of ethanol in breath is about two hundred ten (210) ppm (by volume) with one (1) atmosphere total pressure. For comparison, to determine the concentration of ethanol vapor in a breath sample, law enforcement typically uses an infrared-based instrument that has a one meter (1 m) path length through the breath sample. Although, a longer path length is desirable to improve sensitivity, a ten centimeter (10 cm) path length can be used to detect about ten (10) ppm ethanol in air with a measurement time of a few seconds.

With ten percent (10%) breath in air, the concentration of $CO_2$ is about 0.35% or 3500 ppm. According to one embodiment, an IR band to use with an incandescent lamp as IR source, to avoid saturation, is between 2250 and 2290 cm$^{-1}$ (4.4 µm wavelength). This is the IR absorbance band from $CO_2$ with $O^{16}$ and the less abundant $C^{13}$ isotope, instead of the more abundant $C^{12}$ isotope in natural $CO_2$. According to one embodiment, an IR filter to use is NB-4420-080 nm from Spectrogon.

According to one embodiment, the chemical vapor sensor 10 includes an air input device generally indicated at 16. The air input device 16 includes a plurality of ports, wherein air enters and/or exits the air input device 16, including at least a sample input port 18, a reference input port 20, and an output port 22. According to one embodiment, the air input device 16 can include a motor 24 that is operably connected to an actuator 26, wherein the actuator 26 is aligned with one of the input ports 18,20 in order for air to enter the air input device 16. The motor 24 can be, but is not limited to, operably connected to the actuator 26 by a shaft 25. According to one embodiment, the actuator 26 defines at least one aperture 28, which is aligned with one of the input ports 18,20, such that the air that enters the air input device 16 is from the input ports 18,20 that is aligned with the aperture 28. According to an alternate embodiment, the air input device 16 that controls the flow of air into a sample chamber 30 from the sample port 18, the reference port 20, or a combination thereof, can be a bimetallic strip that is activated by electrical heating.

The output port 22 of the air input device 16 is in fluid communication with the sample chamber 30. According to one embodiment, the sample chamber 30 is an infrared (IR) cell, and can be a length of metal tubing. The sample chamber 30 can be in optical alignment between a light source 34 and a light detector generally indicated at 36. According to one embodiment, the light source 34 is an IR light source. However, it should be appreciated by those skilled in the art that the light source 34 can be other suitable light sources, such as, but not limited to an incandescent lamp.

According to one embodiment, the detector 36 can be a dual-element IR detector, such as, but not limited to, a dual-element thermopile detector that includes a first IR filter 38 and a second IR filter 40. In such an embodiment, the first IR filter 38 can transmit only a band of IR absorbed by carbon dioxide ($CO_2$) and the second IR filter 40 can transmit only a band of IR absorbed by ethanol vapor. According to an alternate embodiment, the detector 36 can be a metal oxide sensor, or other suitable solid-state sensors, wherein the ethanol vapor oscillations can be monitored or detected in the sample chamber 30.

The detector 36 can communicate at least one signal to an analog-to-digital (A/D) converter 42, wherein the output signal from the detector 36 can be conditioned and/or converted for communication to a processor or controller, such as, but not limited to, a microprocessor 44, such that a BAC of the air sample received by the sample input port 18 can be determined, as described in greater detail herein. The microprocessor 44 can include analog and/or digital circuitry that is configured to process sensed signals and determine a BAC, according to one embodiment. Additionally or alternatively, the microprocessor 44 can execute one or more software routines stored in a memory device 45 to determine the BAC.

According to one embodiment, the sample port 18 is the input port, wherein at least a portion of the air in the sample input port 18 contains an exhaled breath of the driver. In such an embodiment, the driver exhales in the direction of the sample input port 18, but does not have to physically contact the sample input port 18, and the reference port 20 is located distant from the driver and other occupants of the vehicle 12 in order to obtain a sample of the ambient air. In operation, the motor 24 actuates the actuator 26 so that the aperture 28 alternates between being aligned with the sample input port 18 and the reference port 20 so that air from the sample input port 18 and the reference input port 20 are continuously, but alternatively, being sampled in the sample chamber 30. In an embodiment, a manifold vacuum or an air pump can create low pressure at the exit port of the sample chamber 30, and thus, draw air from the output port 22. Additionally or alternatively, a device that transmits light through an optical shutter is attached to the shaft 25 that rotates the actuator 26. However, it should be appreciated by those skilled in the art that other suitable systems for measuring or monitoring the position of the actuator 26 can be used, such as, but not limited to, a magnetic measurement system.

According to one embodiment, the chemical vapor sensor 10 should remain clean to operate efficiently and obtain accordance results. Additionally, walls of the chemical vapor sensor 10, including walls of the sample input port 18, the reference input port 20, the sample chamber, or a combination thereof, can remain substantially dry during operation (e.g., operate above a dew point). One or more filters can be used in the chemical vapor sensor 10 to reduce contaminates that reach the sample chamber 30. In one embodiment, the one or more air filters include at least one porous material that passes carbon dioxide and ethanol vapor, but retains organic species that would contaminate walls of the sample chamber 30. To avoid moisture on the walls of the sample chamber 30 or other components of the chemical vapor sensor, one or more electrical heaters can be used to raise the operating temperature of the chemical vapor sensor above a dew point.

Typically, the outputs from the $CO_2$ filter 38 and the ethanol filter 40 can vary as a substantially linear function of the transmitted IR intensity in the respective bands, according to one embodiment. The amplitude of the variation from the $CO_2$ channel ($A_{CO_2}$) is proportional to the $CO_2$ concentration in the mixture of breath and air at the sample input port 18, according to one embodiment. The amplitude of the variation from the ethanol channel ($A_{ETH}$) is proportional to the ethanol concentration of the mixture of breath and air at the sample input port 18. Generally, since the driver's exhaled breath is blown in the direction of the sample input port 18, the concentration of the driver's breath with respect to the ambient air is relatively high, such that the effect of species from other sources that absorb in the same band as ethanol vapor is reduced, and the comparison between the air sampled from the sample input port 18 and the reference input port 20 results in cancellation of a variation from ambient species, according to one embodiment. The BAC of the driver is proportional to the ratio of the measured concentration of ethanol vapor and $CO_2$ in the driver's breath. According to one embodiment, in an approximate linear response, the BAC of the driver is proportional to the ratio of the amplitude of variation from the ethanol channel ($A_{ETH}$) and the amplitude variation from the $CO_2$ channel ($A_{CO_2}$), as represented by the following ratio:

$$\frac{A_{ETH}}{A_{CO_2}}$$

Thus, to determine if the driver is actually providing an appropriate or adequate breath sample, the value of $A_{CO_2}$ can be monitored, such that if $A_{CO_2}$ exceeds a threshold value, then the ratio of the amplitude variation of the ethanol channel and the amplitude of the variation of the $CO_2$ channel is calculated.

According to one embodiment, the light source 34 can be turned on prior to the air sample being taken (e.g., air entering the air input device 16 via the sample input port 18, the reference input port 20, or a combination thereof), before an engine of the vehicle 12 is started, the like, or a combination thereof. For purposes of explanation and not limitation, the light source 34 can be turned on when one of the vehicle's 12 doors are opened, when the vehicle's 12 doors are unlocked, when a potential occupant of the vehicle 12 is sensed near the vehicle (e.g., a key fob is detected), or a combination thereof. Generally, by turning the light source 34 on prior to taking an air sample or before the engine is started, an air sample can typically be taken and analyzed by the chemical vapor sensor system 10 when the driver of the vehicle is positioned to start driving the vehicle 12. Thus, the chemical vapor sensor system 10 does not need to wait for the light source 34 to heat up. Additionally or alternatively, the microprocessor 44 or other suitable controller can turn the light source 34 off under predetermined conditions, so that the light source 34 does not remain on, drawing electrical power, at undesirable times.

According to one embodiment, the person whose breath is being sampled can be informed or indicated when an exhaled breath is sufficient or insufficient for being analyzed by the chemical vapor sensor system 10. Additionally or alternatively, the chemical vapor sensor system 10 can conduct a self-check to ensure that the chemical vapor sensor 10 is sensitive to ethanol. In such an embodiment, the air entering the air input device 16 is from the vehicle's 12 fuel system. The fuel system sample can enter the air input device 16 from either the sample input port 18 or the reference input port 20.

Figure 3A:
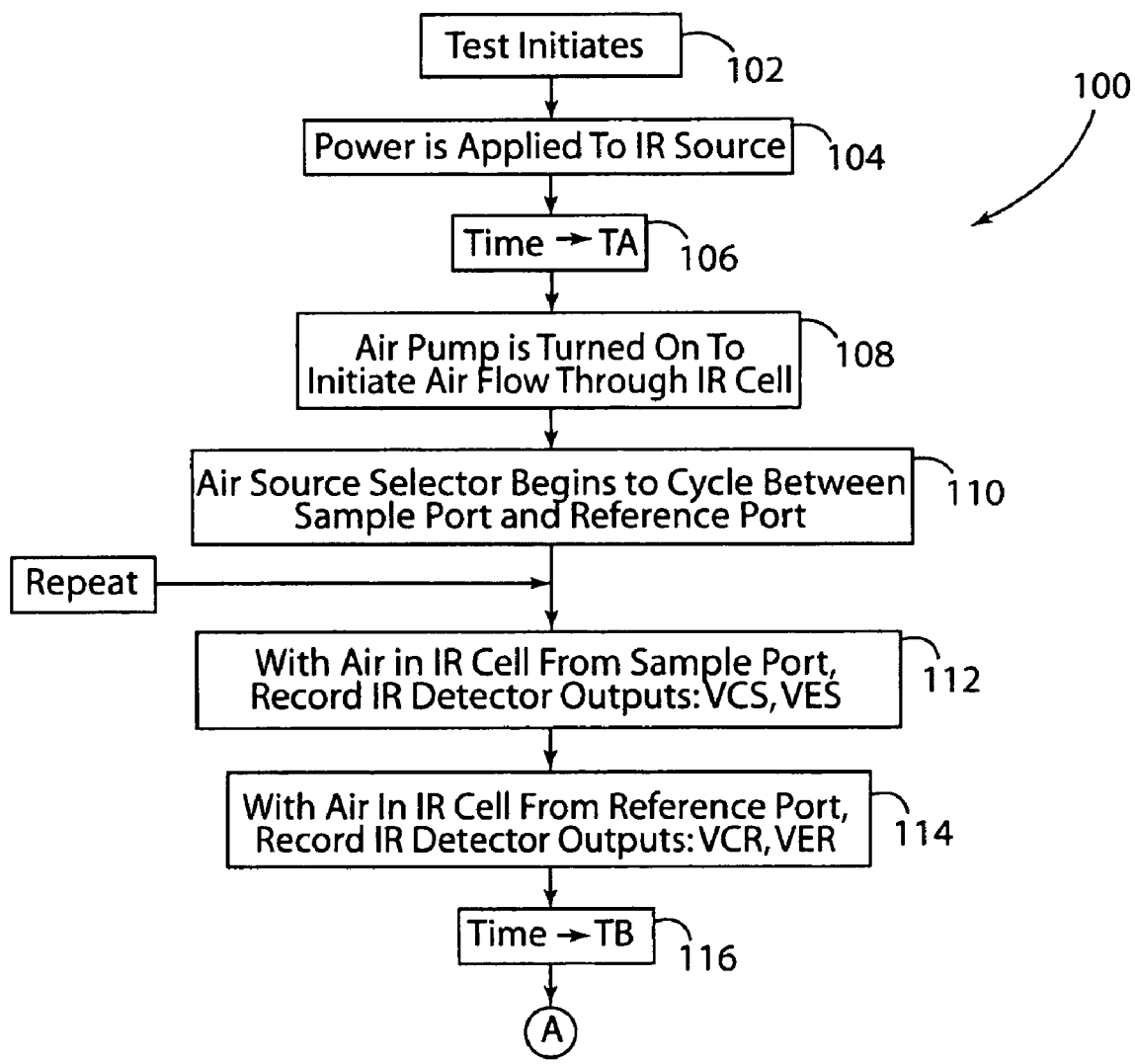
FIGS. 3A and 3B are flow charts illustrating a method of detecting chemical vapors, in accordance with one embodiment of the present invention.
Figure 3B:
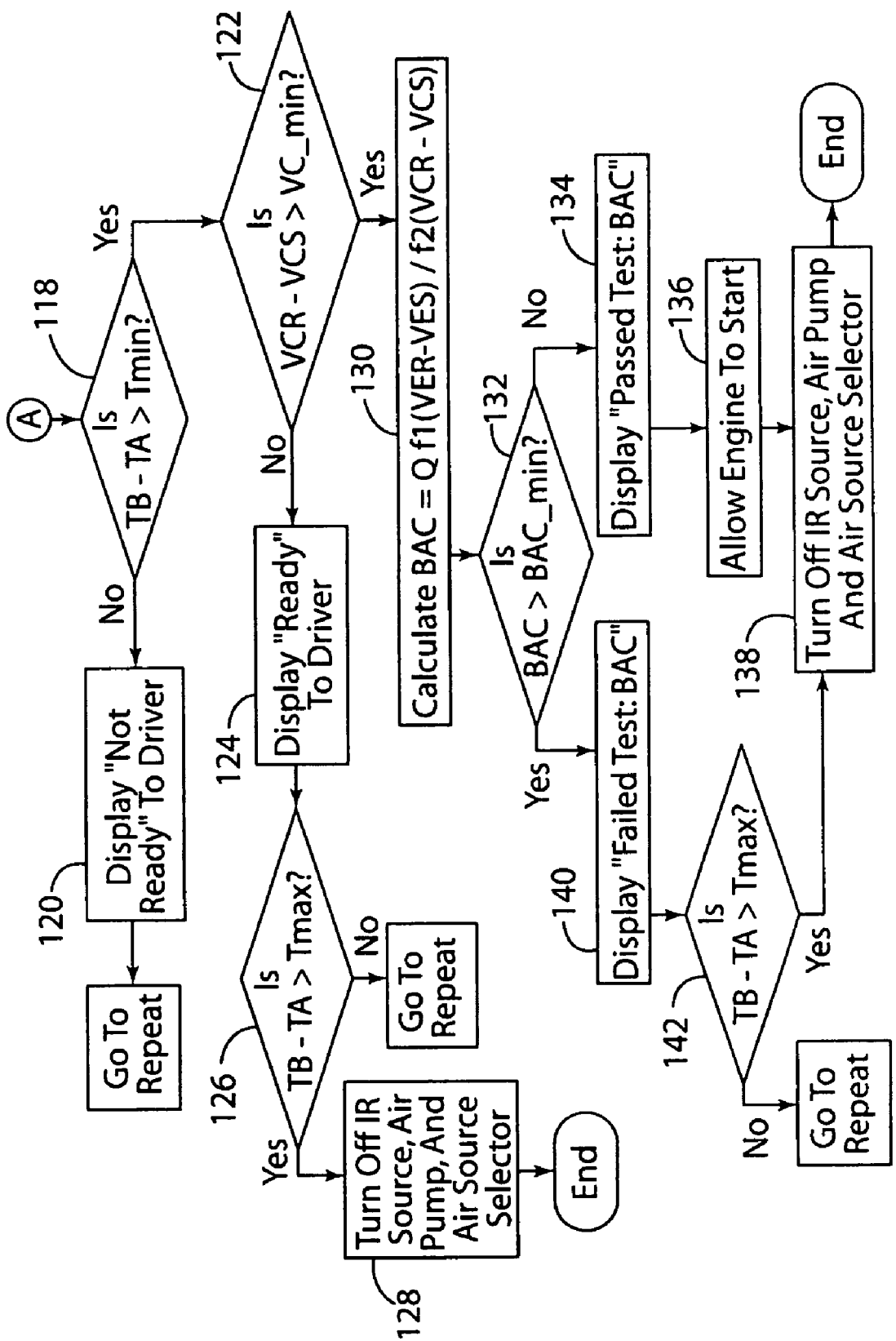

With respect to FIGS. 1-3, a method of sensing a chemical vapor is generally shown in FIG. 3 at 100. The method 100 starts at step 102, wherein the test initiates (e.g., the doors of the vehicle 12 are unlocked or opened, or the like). At step 104, an electrical power is supplied to the light source 34, and at step 106 TA is designated a value. According to one embodiment, TA is the initial reading of a real-time clock once the method 100 has been initiated. Air enters the air input device 16 and the sample chamber 30, at step 108. According to one embodiment, an air pump is used to generate a desired air flow into the air input device 16 and sample chamber 30. At step 110, the air entering the air input device 16 alternates between the sample input port 18 and the reference input port 20. According to one embodiment, the microprocessor 44 or an air source selector commands the motor 24 to actuate the actuator 26, such that the aperture 28 is aligned with the desired input port 18,20.

The method 100 then proceeds to step 112, wherein when the air occupying the sample chamber 30 is a majority of air entered from the sample input port 18, output voltages of the detector 36 are measured, such as, but not limited to a first voltage potential ($V_{CS}$) based upon the $CO_2$ measured by the IR transmitted by the first IR filter 38, and a second voltage potential ($V_{ES}$) based upon the ethanol measured by the IR transmitted by the second IR filter 40. At step 114, when the air occupying the sample chamber 30 is a majority of air entered from the reference input port 20, output voltages of the detector 36 are measured, such as, but not limited to, a third voltage potential ($V_{CR}$) based upon the $CO_2$ measured by the IR transmitted by the first IR filter 38, and a second voltage potential ($V_{ER}$) based upon the ethanol measured by the IR transmitted by the second IR filter 40.

At step 116, TB is designated a value. According to one embodiment, TB is a value based upon the real-time clock subsequent to TA. At decision step 118, it is determined if TB minus TA is greater than $T_{min}$. According to one embodiment, $T_{min}$ is the minimum time after the test or method 100 is initiated in order to substantially ensure the results are accurate. If it is not determined at decision stem 118 that TB minus TA is greater than $T_{min}$, then the method 100 proceeds to step 120, wherein a person is informed that the chemical vapor sensor system 10 is not ready, and the method 100 can then return to step 112. However, if it is determined at decision step 118 that TB minus TA is greater than $T_{min}$, then the method 100 can proceed to decision step 122, wherein it is determined if $V_{CR}$ minus $V_{CS}$ is greater than $VC_{min}$. According to one embodiment, $VC_{min}$ is the difference in voltage potential associated with a minimum breath concentration for a reading to be valid.

If it is determined at decision step 122 that $V_{CR}$ minus $V_{CS}$ is not greater than $VC_{min}$, then the method 100 proceeds to step 124, wherein a person is informed that the chemical vapor sensor system 10 is ready. At decision step 126, it is determined if TB minus TA is greater than $T_{max}$. According to one embodiment, $T_{max}$ is a maximum time allowed for testing or analyzing a person's breath. If it is determined at decision step 126 that TB minus TA is greater than $T_{max}$, then the light source 34, the air pump, the air source selector, the like, or a combination thereof is turned off at step 128, and the method 100 then ends. However, if it is determined at decision step 126 that TB minus TA is not greater than $T_{max}$, then the method 100 returns to step 112.

When it is determined at decision step 122 that $V_{CR}$ minus $V_{CS}$ is greater than $VC_{min}$, then the method 100 proceeds to step 130, wherein the BAC is calculated. According to one embodiment, the calculation of the BAC is represented by the following equation:

$$BAC = Q\left(\frac{f_1(V_{ER} - V_{ES})}{f_2(V_{CR} - V_{CS})}\right)$$

According to one embodiment, $f_1$ is a monotonic function that relates measured voltage potential differences of the ethanol channel to ethanol concentration, $f_2$ is a monotonic function that relates measured voltage potential differences of the $CO_2$ channel to $CO_2$ concentration, and Q is a calibration factor that relates the person's BAC to a ratio of ethanol vapor concentration from a person's breath to a $CO_2$ concentration from a person's breath.

At decision step 132, it is determined if the BAC calculated at step 130 is greater than a $BAC_{min}$. If it is determined at decision step 132 that the calculated BAC is not greater than $BAC_{min}$, then the person whose breath is being analyzed is informed the BAC test has been passed at step 134. According to one embodiment, the vehicle's 12 engine is then allowed to start at step 136. According to an alternate embodiment, the vehicle's 12 engine is allowed to start prior at the BAC test being passed, but the vehicle's 12 transmission cannot be placed into gear prior to the BAC test being passed. It should be appreciated by those skilled in the art that other components or devices of the vehicle 12 can be controlled based upon the results of the BAC test. At step 138, the light source 34, air pump, the air source selector, the like, or a combination thereof are turned off, and the method 100 then ends.

However, if it is determined at decision step 132 that calculated BAC is greater than $BAC_{min}$, then the person is informed that the BAC test has been failed at step 140. At decision step 142, it is determined if TB minus TA is greater than $T_{max}$. If it is determined at decision step 142, that TB minus TA is not greater than $T_{max}$, then the method 100 returns to step 112. When it is determined at decision step 142 that TB minus TA is greater than $T_{max}$, then the method 100 returns to step 138.

Advantageously, the breath of an occupant of the vehicle 12 can be sampled by the chemical vapor sensor system 10 and method 100 to determine the occupant's BAC, without the occupant physically contacting the sample input port 18. Additionally, because the occupant is exhaling in the direction of the sample input port 18, the ethanol contained in the sample breath does not need to be enhanced, as in a passive sensor system. It should be appreciated by those skilled in the art that there may be additional or alternative advantages of the chemical vapor sensor 10 and method 100. It should further be appreciated by those skilled in the art that the above components of the chemical vapor sensor system 10 can be combined in alternative combinations.

The above description is considered that of preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A chemical vapor sensor system comprising:
    an air input device that comprises a plurality of ports comprising:
        a sample input port;
        a reference input port; and
        an output port;
    a light source that emits light;
    a detector in optical communication with said light source that receives at least a portion of said light emitted from said light source;
    a sample chamber in optical communication between said light source and said detector, and in fluid communication with said output port, wherein a actuator coupled to said sample input port and said reference input port operates such that said air alternatively enters said air input device from said sample input port and said reference input port, and enters said sample chamber, whereby alternating samples from the sample input port and the reference input port are present between the light source and the detector; and a processor that receives an output signal from said detector based upon a detection of at least carbon dioxide and ethanol in said air in said sample chamber, wherein said processor determines a blood alcohol content (BAC) of a person whose breath was received in said sample input port based on detecting oscillations of the output signal arising from the alternating samples from the sample input port and the reference input port indicating a portion of air from the sample input port that is exhaled breath.

2. The system of claim 1, wherein said detector is a dual element infrared (IR) detector.

3. The system of claim 2, wherein said dual element IR detector comprises:
a first IR filter adapted to transmit a band of IR absorbed by carbon dioxide; and
a second IR filter adapted to transmit a band of IR absorbed by ethanol vapor.

4. The system of claim 1, wherein a chemical vapor sensor is used with a motor vehicle.

5. The system of claim 1, wherein said BAC is determined by determining a ratio of measured ethanol vapors and carbon dioxide in said person's breath.

6. The system of claim 1, wherein said output signal communicated from said detector varies as a substantially linear function of an intensity of said light emitted from said light source.

7. The system of claim 1, wherein said BAC of said person's breath is determined without said person physically contacting said sample input port.

8. A chemical vapor sensor system comprising:
an air input device that comprises a plurality of ports comprising:
a sample input port;
a reference input port; and
an output port;
an infrared (IR) light source that emits IR light;
a dual element IR detector in optical communication with said IR light source that receives at least a portion of said IR light emitted from said IR light source;
a sample chamber in optical communication between said IR light source and said detector, and in fluid communication with said output port, wherein a actuator coupled to said sample input port and said reference input port operates such that said air alternatively enters said air input device from said sample input port and said reference input port, and enters said sample chamber, whereby alternating samples from the sample input port and the reference input port are present between the light source and the detector; and
a processor that receives an output signal from said dual element IR detector based upon a detection of carbon dioxide and ethanol in said air in said sample chamber, wherein said processor determines a blood alcohol content (BAC) of a person whose breath was received in said sample input port based on detecting oscillations of the output signal arising from the alternating samples from the sample input port and the reference input port indicating a portion of air from the sample input port that is exhaled breath.

9. The system of claim 8, wherein said dual element IR detector comprises:
a first IR filter adapted to transmit a band of IR absorbed by carbon dioxide; and
a second IR filter adapted to transmit a band of IR absorbed by ethanol vapor.

10. The system of claim 8, wherein said BAC is determined by determining a ratio of measured ethanol vapors and carbon dioxide in said person's breath.

11. The system of claim 8, wherein said output signal communicated from said detector varies as a substantially linear function of an intensity of said light emitted from said light source.

12. The system of claim 8, wherein said BAC of said person's breath is determined without said person physically contacting said sample input port.

13. The system of claim 8 further comprising at least one heater to heat an operating temperature of a chemical vapor sensor above a dew point temperature.

14. A method of detecting chemical vapors, said method comprising the steps of:
alternating air samples between a sample chamber and a reference input that are inputted into a sample chamber;
illuminating a light source;
detecting at least a portion of said light emitted from said light source with a detector, wherein said sample chamber is in optical communication between said light source and said detector;
communicating an output from said detector based upon detection of carbon dioxide and ethanol in said air sample; and
determining a blood alcohol content (BAC) of a person whose breath was received in said sample chamber, wherein said BAC is based based on detecting oscillations of the output signal arising from the alternating samples from the sample input port and the reference input port indicating a portion of air from the sample input port that is exhaled breath.

15. The method of claim 14, wherein said step of determining said BAC further comprises determining a ratio of measured ethanol vapors and carbon dioxide in said person's breath.

16. The method of claim 14, wherein said step of determining said BAC further comprises receiving said person's breath without said person physically contacting a sample input port.

17. The method of claim 14, wherein said step of detecting said emitted light further comprises transmitting a band of IR absorbed by carbon dioxide and transmitting a band of IR absorbed by ethanol vapor.

* * * * *